United States Patent [19]
Johnson et al.

[11] Patent Number: 4,755,055
[45] Date of Patent: Jul. 5, 1988

[54] LUMINOMETER CONSTRUCTION

[76] Inventors: Ian R. Johnson, "Winsford" Heol St. Bridget, St. Brides Major, Wales, CF32 OSL; David A. Stafford, 26 Forsythia Drive, Greenways, Cyncoed, Cardiff, Wales; Robert A. Hall, 39 Hambledon Road, Clanfield, Portsmouth, England, PO8 OQS

[21] Appl. No.: 938,522

[22] Filed: Dec. 5, 1986

[30] Foreign Application Priority Data

Dec. 4, 1985 [GB] United Kingdom ................. 8529889

[51] Int. Cl.⁴ ....................... G01N 21/01; G01N 21/13
[52] U.S. Cl. ...................................... 356/440; 356/36; 356/218; 422/52; 422/64
[58] Field of Search ................. 356/218, 36, 240, 440; 250/223 B, 223 R, 458.1, 462.1; 422/52, 63, 64, 65

[56] References Cited

U.S. PATENT DOCUMENTS

| | | | |
|---|---|---|---|
| 2,137,187 | 11/1938 | Stoate | 250/223 B |
| 3,764,214 | 10/1973 | Heiss | 250/458.1 X |
| 4,319,842 | 3/1982 | Priarone et al. | 250/458.1 X |
| 4,385,113 | 5/1983 | Chappelle et al. | 422/52 X |
| 4,421,848 | 12/1983 | Whitlock | 435/8 |
| 4,472,352 | 9/1984 | Quesneau et al. | 422/52 |

FOREIGN PATENT DOCUMENTS

| | | |
|---|---|---|
| 0038134 | 3/1981 | European Pat. Off. . |
| 1330594 | 8/1971 | United Kingdom . |
| 1545538 | 10/1976 | United Kingdom . |
| 2001434 | 7/1978 | United Kingdom . |
| 2073885 | 4/1980 | United Kingdom . |
| 2130744 | 6/1984 | United Kingdom ................ 356/440 |

Primary Examiner—R. A. Rosenberger
Assistant Examiner—S. McGowan
Attorney, Agent, or Firm—Merchant, Gould, Smith, Edell, Welter & Schmidt

[57] ABSTRACT

A luminometer construction including means for supplying samples contained in respective cuvettes 20, in succession to be examined, the cuvettes being introduced into a carrier 10 having a cuvette gripper 19, the carrier 10 defining an examination chamber 21 into which the cuvettes are inserted, the carrier 10 being rotatable between a loading and a test position in which the examination chamber 21 is adjacent to a photo-multiplier device 25, whereby testing of a sample in a cuvette 20 can be carried out, the examination chamber 21 having an edge in a plane inclined to the axis 11 of rotation of the carrier 10, and the photo-multiplier device 25 being arranged with its optical axis 26 perpendicular to such plane.

20 Claims, 6 Drawing Sheets

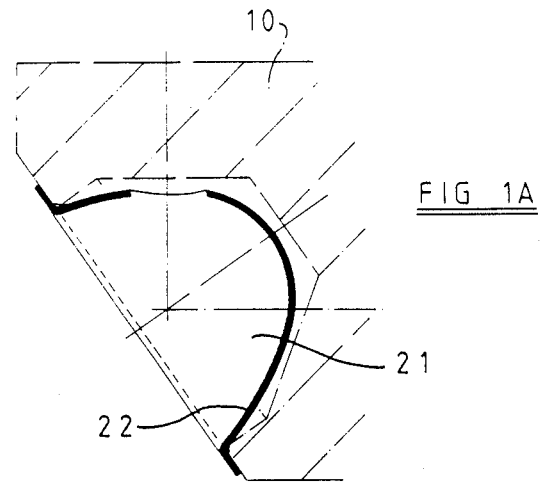
FIG 1A
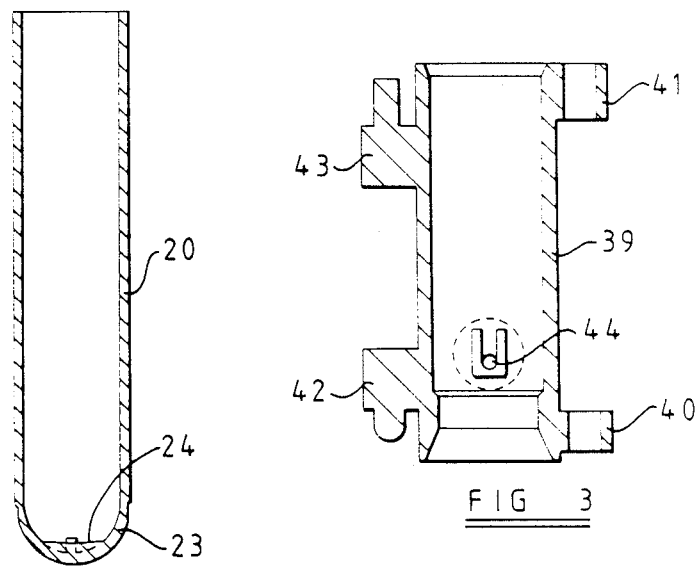
FIG 2
FIG 3

LUMINOMETER CONSTRUCTION

This invention relates to a luminometer construction. A luminometer is a device for measuring light photons, particularly at low light levels, produced by bio-luminescent or chemi-luminescent effects. The luminometer construction with which the invention is concerned is designed to detect and measure light emission produced as a result of chemical or other reactions, the measurement being translated into a signal which may take one of many forms, according to particular tests being undertaken.

Typical circumstances in which the luminometer may be used include testing of samples of liquids to determine various factors and the device may be used in medical applications, in the food and drink, pharmaceutical, water treatment, or other industries. It may also be used for research in various fields.

The luminometer has means for presenting a sample, usually as a liquid or a liquid suspension, to a photo-multiplier device by means of which the actual measurement is carried out.

It may be necessary to prepare the sample before presentation to the photo-multiplier device, in various ways, depending upon the nature of the sample and upon the requirements of the test to be conducted. This preparation may include extraction of ATP (adenosine-5'-triphosphate) molecules, adding suitable reagents or other processes to produce light emissions of sufficient intensity to be detectable and measurable by the photo-multiplier device. It is also possible to carry out certain functions while the sample is presented to the photo-multiplier device.

A number of methods have been devised for presenting samples to the photo-multiplier, which is extremely sensitive and must be screened against extraneous influences. The requirement for examination of a large number of samples in succession has resulted in the development of various systems for bringing the samples to the apparatus in a conveyor arrangement, each sample being presented in turn for examination and then returned to the conveyor arrangement. The samples are, in such a system, contained in individual transparent cuvettes, which are placed, in turn, into a chamber which is open, or in communication, at least at an appropriate time, to the photo-multiplier.

There are certain problems to be overcome in introducing and removing cuvettes from the chamber with which the photo-multiplier communicates. In particular, stray extraneous light or other discharges must be excluded from the chamber during the test period, since these could adversely affect the accuracy of detection of the light photons, by the photo-mulitplier, and yet the cuvettes must be easily and quickly introduced into the chamber and removed from it, preferably without the need for elaborate screening means. Light collection must be maximised within the chamber in order to provide the best possible conditions for accurate measurement.

It is the object of the invention to provide a luminometer construction which enables samples to be readily examined in turn and in which the accuracy of the results is high.

In accordance with the present invention, there is provided a luminometer construction including means for supplying samples, contained in respective individual cuvettes, in succession to be examined, to a carrier, whereby they are presented in turn to a photo-multiplier device, the carrier comprising a rotatable structure having a portion defining an examination chamber, and a cuvette gripper arranged to hold a cuvette in a position such that a sample containing portion thereof is within the examination chamber, and the carrier being rotatable between a loading position in which the cuvettes can be inserted into the gripper and a test position in which the chamber is positioned adjacent to the photo-multiplier device.

Preferably the carrier is mounted for rotation about an axis and the cuvette gripper is arranged for insertion of cuvettes in a direction substantially parallel with that axis, the examination chamber being formed in the side of the carrier with an external edge in a plane inclined to the said axis and the photo-multiplier device being positioned with its own optical axis perpendicular to the said plane of the edge of the examination chamber.

Conveniently therefore, the examination chamber is in the form of a concave recess or cavity in the side of the carrier, having an edge conforming generally to the shape of the adjacent end of the operative part of the photo-multiplier device.

The chamber has a single hole through which a cuvette, in use, can extend whereby in the test position, the centre line of the cuvette intersects the optical axis of the photo-multiplier device at a position close to the said plane of the edge of the examination chamber.

With this arrangement the cuvette base containing a sample is, in use, positioned close to the photo-multiplier device and on its axis, so that the collection of light photons is optimised.

The cuvette gripper is preferably situated in a position enabling cuvettes to be introduced through the examination chamber and into the single hole referred to, the cuvettes being withdrawn also in the opposite direction, the examination chamber being shaped and positioned to allow for the introduction and withdrawal of cuvettes without necessity for other holes or cut-outs for the passage of the cuvettes.

The angle of the plane of the edge of the examination chamber, relatively to the axis of rotation of the carrier is preferably 35°, in order to enable the cuvettes to be conveniently introduced and withdrawn.

The cuvettes may be brought to and carried away from the luminometer by a conveyor arrangement. This may include a number of individual holders which may be brought into the cuvette loading position in turn, a cuvette being extracted from the holder and transferred into the cuvette gripper, the carrier then being rotated to bring the cuvette into the test position and after testing, the carrier being again rotated to the loading position at which the cuvette is returned to its holder.

The holders may be interconnected to make up a bandolier which is driven in steps to present successive cuvettes to the instrument for test, in turn.

A drive mechanism is conveniently provided to drive the cuvette holders in sequence with rotational movements of the carrier and with means for transferring cuvettes from their holders into the cuvette gripper and returning them thereto.

A controller may be provided which is capable of controlling functions of the luminometer or of equipment associated with the luminometer, including identification of a sample provided, setting up or adjusting the luminometer in preparation for a particular test, controlling sample preparation operations, actuation of sample handling equipment, energisation of the photomultiplier device, and processing of data provided, in use, from the photo-multiplier device to provide an output in a required form.

The controller preferably includes software which is dedicated to a particular test to be carried out and conveniently carries out all necessary functions to produce a test result.

Preferably also, the controller includes a means for monitoring the photo-multiplier device. By this means, accuracy of measurement can be maintained at a high level.

Functions carried out by the controller may be performed by apparatus within the luminometer construction or externally thereof.

The invention will now be described by way of example with reference to the accompanying drawings in which:

FIG. 1a is an enlarged sectional view of the chamber forming part of the luminometer carrier;

FIG. 2 is an enlarged cross-section of a cuvette;

FIG. 3 is a similarly enlarged cross-section of a cuvette holder;

Figure 1:
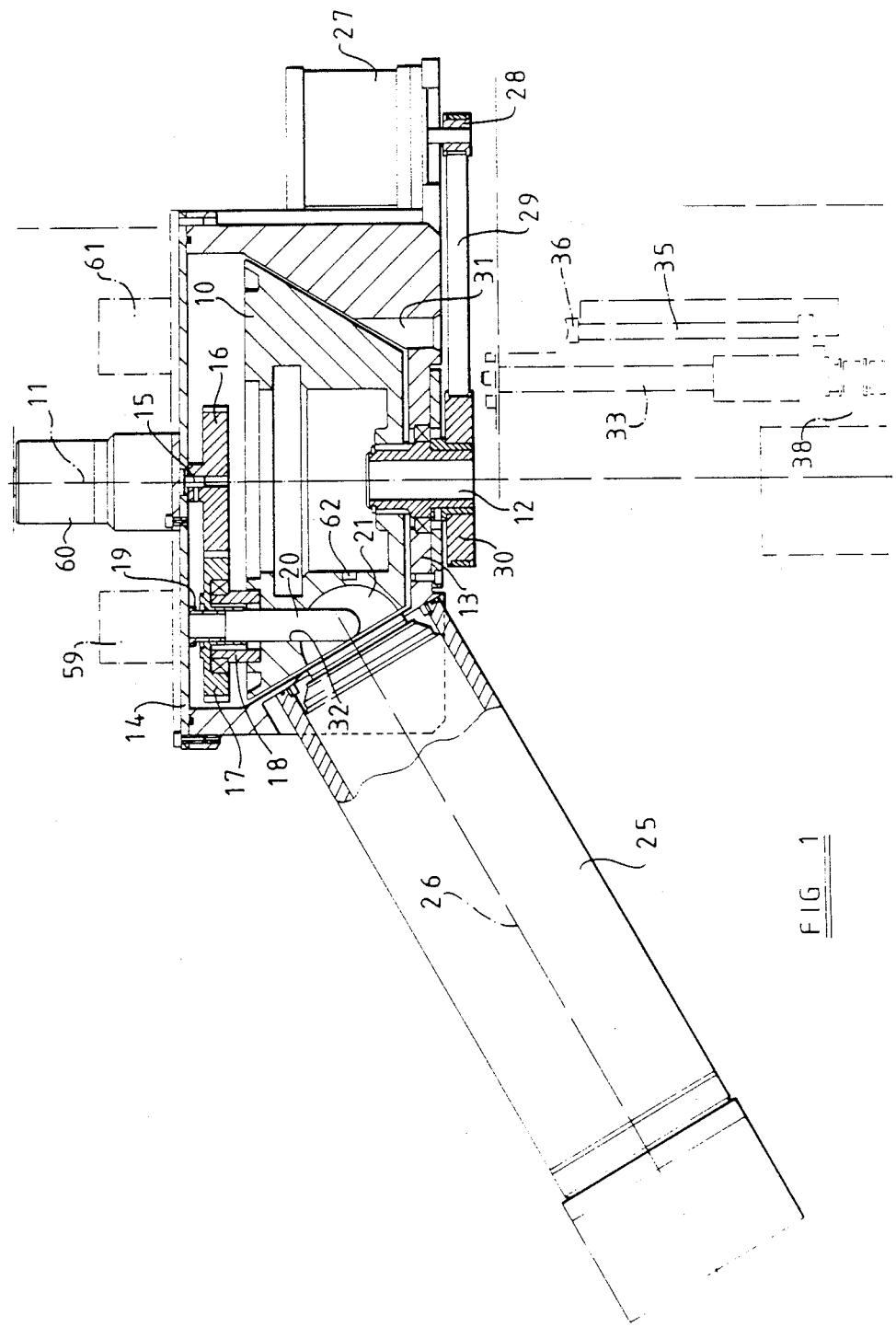
FIG. 1 is a view of a luminometer construction according to the invention.

FIG. 1 shows a luminometer construction intended for the test of liquids or liquid suspensions, and wherein the substances are contained within individual transparent cuvettes which are brought to the instrument in turn. The substance may be subjected to processes which may be bio-luminescent or chemi-luminescent, creating emission of light photons which are detected by a photo-multiplier device in the instrument.

The drawing shows a rotatable carrier 10 in the form of a bowl mounted for rotation about a vertical axis 11. The bowl is mounted on a short shaft 12 which is carried on a fixed structure 13. The fixed structure is shown as an outer bowl with a lid 14 carrying a shaft 15, the centre of which is also on the axis 11. The shaft 15 has a gear 16 which is below the lid 14 and therefore within the space also occupied by the bowl 10. The gear 16 meshes with a gear 17 journalled by means of a hollow shaft 18 fixed in the upper part of the bowl 10. Within the hollow shaft is a cuvette gripper 19 for gripping a cuvette 20, to which reference will be made later.

The bowl 10 has a generally frustoconical shape with the narrower end downwards and connected to the short shaft 12. The circular side of the bowl is therefore inclined downwardly and the angle of the inclination, in this example, is 35° with respect to the vertical axis 11. At one point, in the side of the bowl, there is defined an examination chamber 21 which is also shown in FIG. 1a. This has concave form, the profile being generally ellipsoidal. The internal surface is reflective as indicated at 22. The edge of the chamber 21 is therefore generally circular and is substantially in a plane which is inclined at 35° to the vertical axis 11.

The cuvette 20, as shown in FIG. 1, can extend into the examination chamber 21. The cuvette as shown in FIG. 2 is a small transparent test tube having one end closed to form a generally hemi-spherical end portion 23. Cuvettes may be made from polystyrene. In the example shown, there are, within this end portion, moulded ribs 24 which aid agitation of the contents. These could be omitted, if not required.

As seen in FIG. 1, the cuvette is positioned so that the centre of the hemi-spherical end 23 coincides with the cusp of the ellipse formed by the examination chamber 21. This is spaced from the plane defined by the edge of the chamber by a distance approximating to the external radius of the hemi-spherical end of the cuvette.

Positioned adjacent to the chamber 21 when it is in the test position as shown in FIG. 1 is a photomultiplier tube device 25. This is of highly sensitive type and requires to be screened from extraneous light or other discharge sources. It is therefore positioned within the outer structure 13 in a manner sealed from external light emissions.

The optical axis 26 of the photo-multiplier tube is perpendicular to the plane of the edge of the chamber and is therefore coincident with the central axis of the ellipse formed by the chamber 21. It can be seen from FIG. 1 that when a cuvette 20 is in the test position as shown, the hemi-spherical end of the cuvette is very close to the operative end of the photo-multiplier tube and the axes of the cuvette and of the photo-multiplier tube optical system intersect.

The bowl 10 is rotatable within the fixed structure 13 and to carry out such rotation an electric motor 27 is provided. This carries a pulley 28, driving belt 29, engaging over a further pulley 30 which is carried on the short vertical shaft 12 for the bowl 10.

Figure 6:
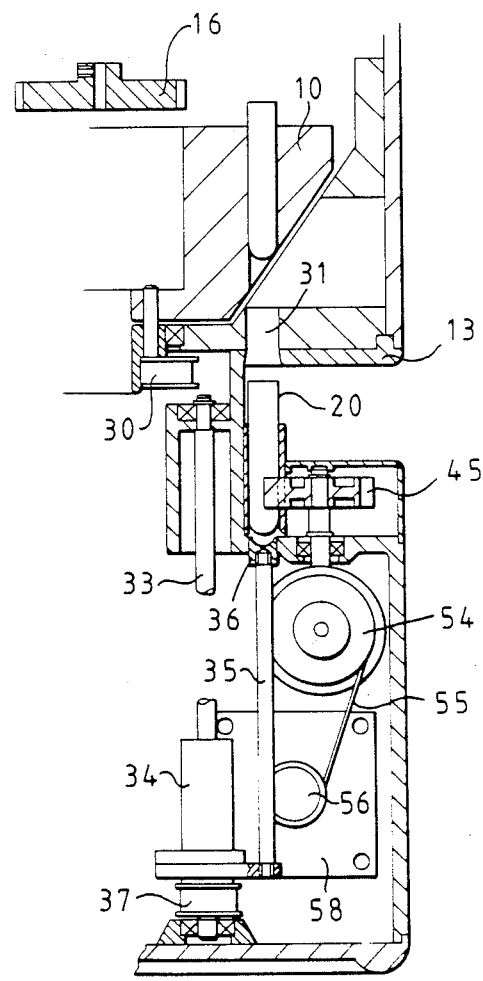
FIG. 6 is a further view of the said drive mechanism.

The bowl 10 is arranged to be rotated through 180° between a cuvette loading position and the test position shown in FIG. 1. FIG. 6 shows a cuvette 20 ready to be loaded into the bowl. To load, the cuvettes are lifted vertically to pass through a hole 31 in the fixed structure 13. It is possible to load a cuvette only when the chamber 21 is in the load position, that is, in register with the hole 31. The angle of the edge of the chamber 21 is such that the cuvette will pass the lower extremity of that edge with a small clearance. The cuvette is lifted so that its upper end registers with a hole 32 in the top of the chamber 21 and this is aligned with the gripper 19. Although not shown, there is a short flared extension aligned with the hole 32 and protruding a short way into the chamber 21. This provides a lead-in for cuvettes. However, it does not adversely affect the reflector characteristics to any significant extent. The cuvette is therefore lifted vertically and passes into the chamber 21 and thence through the hole 32 into the gripper 19. The cuvette occupies a position such that when the bowl is indexed or rotated to the test position, the cuvette occupies the location shown in FIG. 1 and described hereinbefore.

To lift a cuvette, there is a lifting mechanism shown particularly in FIG. 6. This comprises a vertical rotatable shaft 33, having its ends mounted in bearings in a fixed frame forming part of the structure 13. The shaft 33 is screw threaded and a ball nut assembly 34 is engaged on the shaft so that when the shaft is rotated, the ball nut assembly 34 will lift. An arm on the ball nut assembly carries a vertical push rod 35 to the top of which is secured a pusher pad 36 which can engage underneath a cuvette 20 to lift it vertically into the loaded position. To rotate the shaft 33 and thus lift the ball nut, push rod, and pusher pad assembly, a pulley 37 is secured to the lower end of the shaft. This is driven through a belt drive indicated in outline in FIG. 1 at 38.

The cuvettes are brought to the luminometer by a conveyor arrangement which comprises a bandolier made up from a number of interconnected cuvette holders, one of which is shown in FIG. 3. The holder 39 is a small tubular moulding with four integral lugs. One pair of lugs 40, 41, form sockets and the other two lugs 42, 43, carry pins to engage in sockets in an adjacent cuvette holder. The lug 40 is a hollow eye, whereas the lug 41 is hook-shaped. The lug 42 has a small circular spigot and the lug 43 has a flattened spigot. It is possible to join adjacent cuvette holders together by engaging the lugs. The lugs 40, 42, are engaged by dropping the pin into the socket, and the pin on the lug 43 can be engaged laterally in the hook-shaped lug 41. By this means it is possible to build up a bandolier of cuvette holders of any desired length. The individual cuvettes are engaged in their holders by friction, and in the side of the cuvette holder 39 there is a resilient detent 44 which is pressed aside when a cuvette is entered into the holder and which serves to provide the frictional resistance against release of the cuvette out of the holder. However, when the pusher assembly engages and pushes up on the bottom of a cuvette, it will readily slide out of the holder.

Figure 4:
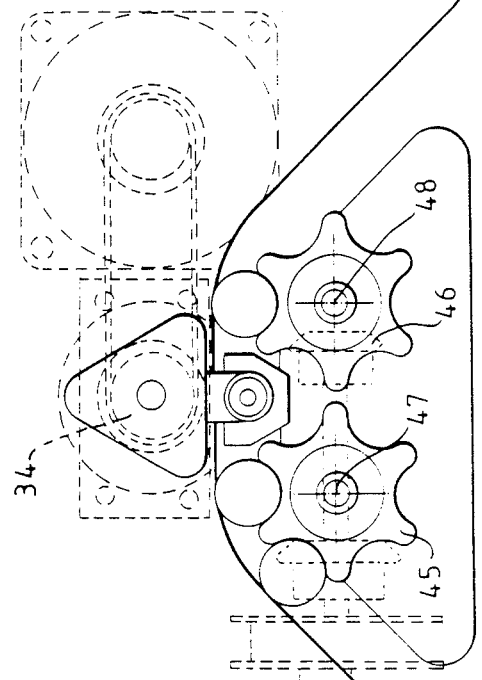
FIG. 4 is a diagrammatic plan view of part of the bandolier drive mechanism.
Figure 5:
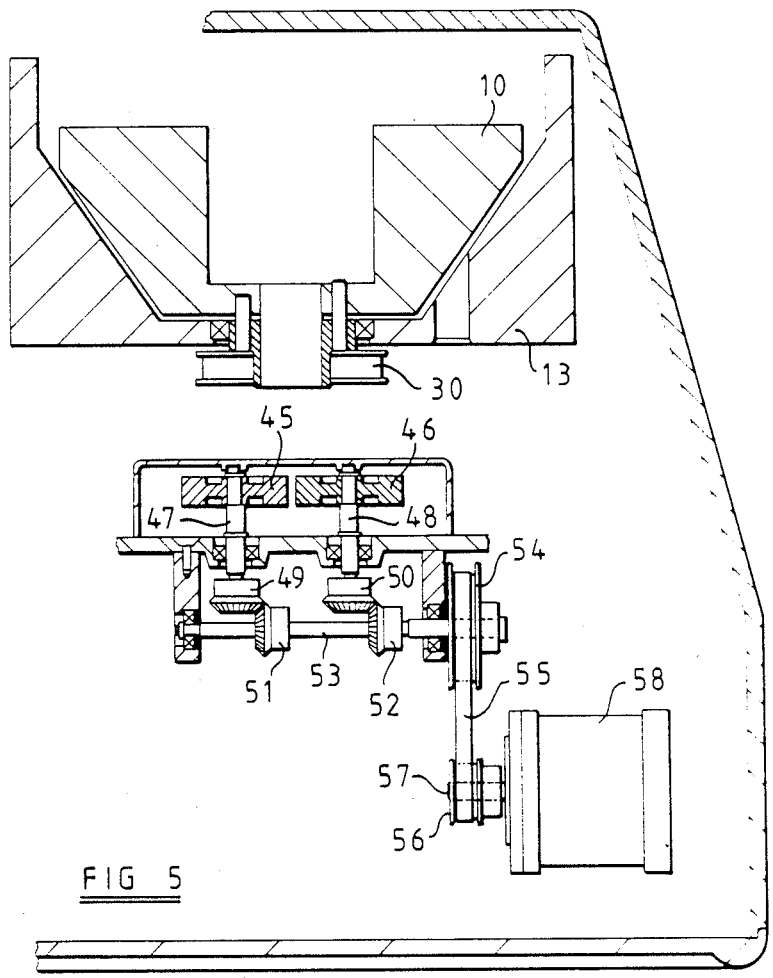
FIG. 5 is a side view showing the drive mechanism.

The cuvette holders 39 are driven, in turn, by means of a mechanism shown in FIGS. 4, 5, and 6. Two vertically mounted star wheels 45, 46, are carried on respective vertical shafts 47, 48. To the lower end of each of these is secured a bevel gear 49, 50, engaging with respective bevel gears 51, 52, on a common shaft 53. The shaft 53 carries a pulley 54 engaged by a belt 55, also passing over a pulley 56 on a motor shaft 57 of a motor 58.

The star wheels 45, 46, are relatively close together and have lobes which can engage between the cuvette holders 39 in the bandolier. This arrangement is shown in outline in FIG. 4. The cuvettes are brought in their holders in turn to the loading position which is in the centre between the two star wheels 45, 46, and at this position the pusher assembly lifts the cuvettes as already described.

In the top of the luminometer a liquid handling system is positioned. This may be used to inject measured quantities of reagents and/or samples of other substances directly into the cuvettes, as may be required, while the cuvettes are presented to the photo-multiplier device or at other positions. The system is generally identified in the drawings at 59.

The shaft 15 in the centre of the top of the lid 14 may carry an agitator device 60 which drives through the gears 16, 17, which carry the cuvette gripper already described. This serves to agitate the sample to ensure adequate mixing and thus uniformity of the emission of light photons.

To extract the cuvettes from the bowl when tests have been carried out, a device 61 is provided. This includes a pusher arranged to drive cuvettes downwardly into engagement with their respective holders.

The construction includes appropriate electrical circuits whereby the sample handling apparatus is actuated in the required sequence.

The three main sub-assemblies, comprising the bowl and its housing and the associated parts, the cuvette lift mechanism, and the bandolier system, are all mounted on a common base and are so connected that movement between assemblies is prevented, in order to ensure accuracy of operation and thus reliability of result. A suitable cabinet may enclose all the assemblies.

Figure 7:
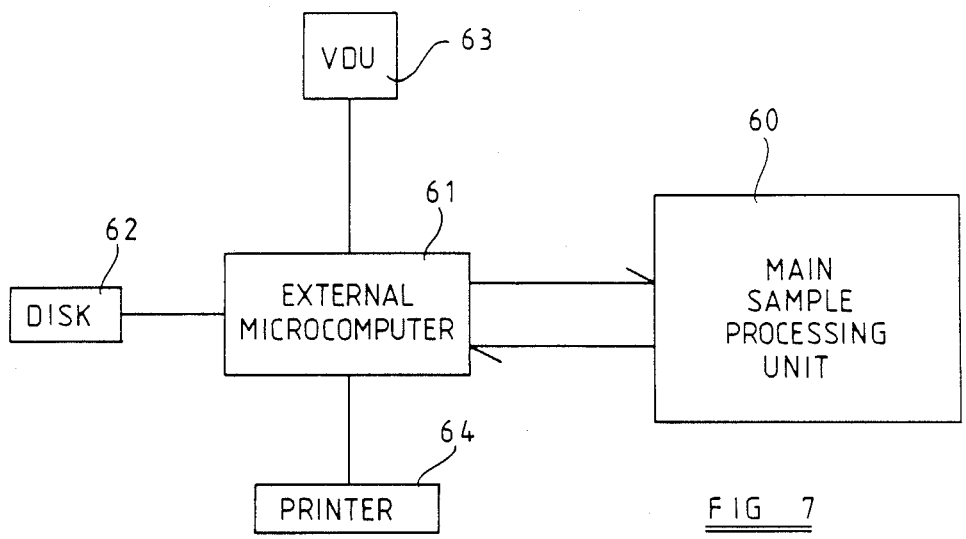
FIG. 7 is a diagrammatic representation of a luminometer system in accordance with the invention.

FIG. 7 shows in diagrammatic form, a system layout in which the main sample processing unit which comprises the luminometer construction and its cuvette supply system, is connected to a controller, which is this case includes a micro-computer 61 to which are connected a disc drive 62, a display unit (VDU) 63, and a printer 64.

Figure 8:
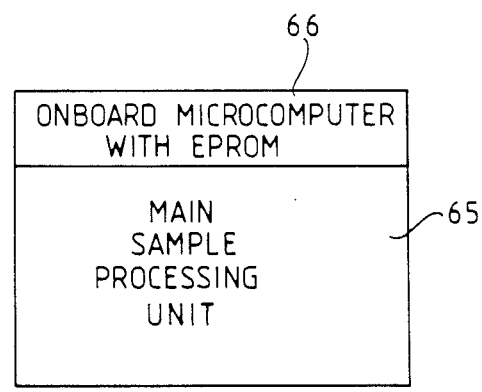
FIG. 8 is a diagrammatic representation of an alternative luminometer system.

FIG. 8 shows an alternative arrangement in which the main sample processing unit 65 is provided with an onboard micro-computer 66, which is controlled through an EPROM.

In operation, the cuvettes, containing samples, are brought to the apparatus by the bandolier system described. Prior to measurement in the luminometer, the samples may undergo pretreatment. Several pretreatment processes, such as incubation, injection of reagents, and mixing at several possible positions, may be available under control of protocol software.

A convenient arrangement involves calibration by testing the first five or so samples which would contain a serial solution of ATP standards. This ATP concentration is to be determined by interpolation from a standard curve. Sample concentration can be compared also by spiking with a known ATP concentration.

After setting up the standard, analysis of samples is continuous, so that samples will be analysed before data collection commences.

Cuvettes are brought to the luminometer by the bandolier system as described, and each cuvette occupies, for the time being, a position in the centre between the two star wheels 45, 46, as indicated in FIG. 4. When the cuvette is in such position, the lifting mechanism is actuated and the pusher pad 36 lifts the cuvette into the bowl 10 which, at that time, has the chamber 21 positioned in alignment with the cuvette. When a cuvette has been loaded and is gripped in the gripper device 19, the bowl 10 is rotated through 180° to bring the chamber 21 into alignment with the photo-multiplier device 25. The injector device 59 may be actuated, if required, to inject appropriate quantities of reagents or other substances and the vibrator 60 may be actuated to agitate the contents of the cuvette. Light photons which are emitted from the sample are detected by the photo-multiplier device 25.

One arrangement is that when all samples in a batch have been tested, the computer program will return to a menu from which the operator may call for data analysis in various forms, such as a graphic representation on the VDU and a printout. A self diagnostic program may be run continuously within the apparatus and all control may be through appropriate software.

The shape of the chamber 21, as well as the positioning of the cuvette in relation to the photomultiplier device, optimises the collection of light photons with minimum loss of such light.

When the test on a sample has been carried out, the cuvette is returned to the loading position by again rotating the bowl 10 through 180°. The ejector device 61 is then actuated to push the cuvette down again into its cuvette holder in the bandolier. The drive mechanism now advances the bandolier by one space.

Conveniently, electrical stepping motors may be used for some or all of the functions.

It is possible to raise the temperature of the substance within the cuvette in the test position and, for this purpose, heating means, indicated generally at 62, is provided adjacent to the chamber 21 and in the bowl 10. If required, a cooling system may be used for cooling the photo-multiplier device 25. Piezo-electric, or other systems are suitable. This can ensure accurate temperature control of the operative portion of the photo-multiplier device 25, thus ensuring accuracy.

The controller, which may include or comprise a computer or equivalent device as already described, may be provided to control the apparatus itself as well as, if appropriate, other associated equipment.

Included also is means for preparing the sample, including ATP extraction, reagent adding, temperature regulation, mixing, or other functions appropriate to the test being carried out. In some cases light emission may be produced prior to presentation of the sample to the test position. Timing devices may also be actuated to bring the sample to the test position at a correct time in relation to initiation of the light emissions. These functions may be carried out within or externally of the instrument.

The controller software also preferably includes means for actuating the instrument, including the sample handling apparatus for introducing and extracting the samples, and also the photo-multiplier energisation, and other apparatus.

The signal produced by the photo-multiplier device is also processed to provide an output in any required form.

The controller software is preferably dedicated to the particular test to be conducted, and is capable of controlling all functions from first sample identification to output readout, or other output. As seen in FIG. 8, the whole apparatus may be in one unit which is conveniently protected against external influences, even in a relatively hostile environment. For example, a liquid substance to be tested, such as milk, may be introduced and a signal provided which may indicate a result in numerical or other form or in its simplest form, an indication of acceptance or rejection. The apparatus may therefore be capable of use by an unskilled operative.

In an example in which the apparatus is used with a continuous process, such as in a food processing plant or activated sludge treatment plant, the output signal may be arranged for transmission to a control unit, whereby, in the event of testing of a sample which is unsatisfactory in a predetermined way, the whole process is stopped. Other feed back, on line, uses can also be adopted.

On the other hand, the apparatus may be used for research in various fields, and in such circumstances an operator may be able to control variables including the sample preparation phase, photo-multiplier performance, or subsequent data processing of the output signal.

We claim:

1. A luminometer construction including means for supplying samples, contained in respective individual cuvettes 20, in succession to be examined, to a carrier 10, whereby they are presented in turn to a photo-multiplier device 25, characterised in that the carrier 10 comprises a rotatable structure having a portion defining an examination chamber 21, and a cuvette gripper 19 arranged to hold a cuvette 20 in a position such that a sample containing portion thereof is within the examination chamber 21, and the carrier 10 being rotatable between a loading position in which cuvettes 10 can be inserted into the gripper 19, and a test position in which the chamber 21 is positioned adjacent to the photo-multiplier device 25.

2. A luminometer construction as claimed in claim 1, characterised in that the carrier 10 is mounted for rotation about an axis 11, and the cuvette gripper 19 is arranged for insertion of cuvettes 20 in a direction substantially parallel with that axis 11, the examination chamber 21 being formed in the side of the carrier 10 with an external edge in a plane inclined to the said axis 11, and the photo-multiplier device 25 being positioned with its own optical axis 26 perpendicular to the said plane of the edge of the examination chamber.

3. A luminometer construction as claimed in claim 2 characterised in that the examination chamber 21 is in the form of a concave cavity in the side of the carrier 10, having an edge conforming generally to the shape of the adjacent end of the operative part of the photo-multiplier device 25.

4. A luminometer construction as claimed in claim 3 characterised in that the chamber 10 has a single hole 32 through which a cuvette 20, in use, can extend, whereby in the test position, the centre line of the cuvette 20 intersects the optical axis 26 of the photo-multiplier device 25 at a position close to the said plane of the edge of the examination chamber 21.

5. A luminometer construction as claimed in claim 2 characterised in that the angle of the plane of the edge of the examination chamber 21, relatively to the axis 11 of rotation of the carrier 10 is 35°, and the hole for introduction of cuvettes is positioned to allow cuvettes to be introduced or withdrawn in a direction parallel with the said axis 11 of rotation of the carrier 10.

6. A luminometer construction as claim in claim 5 characterised by a conveyor arrangement for supplying cuvettes 20 to, and removing cuvettes from the apparatus.

7. A luminometer construction as claimed in claim 6 characterised in that the conveyor arrangement includes a plurality of individual holders 39 arranged to be brought into the cuvette loading position in turn, a cuvette 20 being extracted from the holder 39 and transferred into the cuvette gripper 19, the carrier 10 then being rotated to bring the cuvette 20 into the test position, and after testing, the carrier 10 being again rotated to the loading position at which the cuvette 20 is returned to its holder 39.

8. A luminometer construction as claimed in claim 7 characterised in that the holders 39 are interconnected to make up a bandolier which is driven in steps to present successive cuvettes 20 to the instrument for test, in turn.

9. A luminometer construction as claimed in claim 8 characterised by a drive mechanism to drive the cuvette holders 39, in sequence with rotational movements of the carrier 10 and with means for transferring cuvettes 20 from their holders into the cuvette gripper 19 and returning them thereto.

10. A luminometer construction as claimed in claim 7 characterised by a drive mechanism to drive the cuvette holders 39, in sequence with rotational movements of the carrier 10 and with means for transferring cuvettes 20 from their holders into the cuvette gripper 19 and returning them thereto.

11. A luminometer construction as claim in claim 10 characterized by a controller capable of controlling functions of the luminometer and of equipment associated with the luminometer, including identification of a sample provided, setting up or adjusting the luminometer in preparation for a particular test, controlling sample preparation operations, actuation of sample handling equipment, energisation of the photo-multiplier device 25, and processing of data provided, in use, from the photo-multiplier device 25 to provide an output in a required form.

12. A luminometer construction as claimed in claim 10 characterised in that the controller includes software which is dedicated to a particular test to be carried out and conveniently carries out all necessary functions to produce a test result.

13. A luminometer construction as claimed in claim 12 characterised in that the controller includes a means for monitoring the photo-multiplier device 25.

14. A luminometer construction as claimed in claim 11 characterised in that the controller includes a means for monitoring the photo-multiplier device 25.

15. A luminometer construction as claimed in claim 14 characterised b y an injector 59 for injecting materials into samples held in cuvettes when in the test position.

16. A luminometer construction as claimed in claim 15 characterised by an agitator, whereby the contents of cuvettes 19 can be agitated.

17. A method of testing samples in a luminometer construction comprising supplying samples, contained in respective individual cuvettes 20, in succession, to a carrier 10, characterised in that the carrier 10 is rotated from a cuvette loading position, to a test position in which the cuvette is disposed within an examination chamber 21 formed in the carrier 10, actuating a photo multiplier device 25 to which a sample containing portion of the cuvette 20 is exposed within said examination chamber 21, analysing the signal received from the photo-multiplier device 25, and returning the cuvette 20 to the loading position, unloading the cuvette 20 in readiness for the supply of a further cuvette 20.

18. A method of testing as claimed in claim 17 characterised in that the sample is subjected to pretreatments.

19. A method of testing as claimed in claim 18 characterised in that sample analysis is carried out in comparison with a standard.

20. A method of testing as claimed in claim 17 characterised in that sample analysis is carried out in comparison with a standard.

* * * * *